United States Patent
Stull

(10) Patent No.: US 9,138,344 B2
(45) Date of Patent: *Sep. 22, 2015

(54) APPARATUS AND METHOD OF GASTRIC COOLING USING BALLOON CATHETER

(71) Applicant: ZOLL CIRCULATION, INC., San Jose, CA (US)

(72) Inventor: Paul M. Stull, Bodega Bay, CA (US)

(73) Assignee: Zoll Circulation, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/181,297

(22) Filed: Feb. 14, 2014

(65) Prior Publication Data
US 2014/0277304 A1 Sep. 18, 2014

Related U.S. Application Data

(63) Continuation of application No. 13/037,224, filed on Feb. 28, 2011, now Pat. No. 8,652,190, which is a continuation of application No. 11/474,590, filed on Jun. 26, 2006, now Pat. No. 7,896,009, which is a continuation of application No. 10/051,870, filed on Jan. 16, 2002, now Pat. No. 7,077,825.

(51) Int. Cl.
*A61F 7/00* (2006.01)
*A61F 7/12* (2006.01)

(52) U.S. Cl.
CPC ......... *A61F 7/123* (2013.01); *A61F 2007/0022* (2013.01); *A61F 2007/0054* (2013.01); *A61F 2007/0056* (2013.01); *A61F 2007/0095* (2013.01)

(58) Field of Classification Search
CPC ............. A61F 7/00; A61F 7/12; A61F 7/123; A61F 2007/0022; A61F 2007/0054; A61F 2007/0055; A61F 2007/0056
USPC ........................ 607/96, 104–107; 606/27, 28; 604/93.01, 113
See application file for complete search history.

(56) References Cited

U.S. PATENT DOCUMENTS

| | | |
|---|---|---|
| 1,011,606 A | 12/1911 | Fulton |
| 2,058,780 A | 10/1936 | Elliott |

(Continued)

OTHER PUBLICATIONS

Taber, "Gastric Lavage"; Taber's Cyclopedic Medical Dictionary, ed. 18 (1997); pp. 777-778.

(Continued)

*Primary Examiner* — Ahmed Farah
(74) *Attorney, Agent, or Firm* — John K. Fitzgerald; Rutan & Tucker, LLP

(57) ABSTRACT

A balloon catheter is used in a closed-loop heat exchange system for manipulating the temperature of a patient. The balloon catheter is positioned in the stomach of the patient, and then expanded with a heat exchange fluid delivered through a lumen formed in the shaft of the catheter. The balloon catheter comes into contact with the wall of the stomach, and the stomach substantially conforms around the expanded balloon catheter. The heat exchange fluid is allowed to flow continuously into and out of the balloon catheter. Heat is exchanged between the balloon catheter and the stomach so as to controllably alter the temperature of at least a portion of the patient. Anti-shivering mechanisms and automatic control based on temperature feedback from the patient may be used in connection with the heat exchange system.

12 Claims, 5 Drawing Sheets

(56) References Cited

U.S. PATENT DOCUMENTS

| | | | |
|---|---|---|---|
| 2,148,541 | A | 2/1939 | Dierker |
| 2,466,042 | A | 4/1949 | Reich et al. |
| 3,125,096 | A | 3/1964 | Antiles et al. |
| 3,369,549 | A | 2/1968 | Armao |
| 3,425,419 | A | 2/1969 | Dato |
| 3,460,538 | A | 8/1969 | Armstrong |
| 3,738,372 | A | 6/1973 | Shioshvili |
| 3,768,484 | A | 10/1973 | Gawura |
| 3,776,241 | A | 12/1973 | Swift et al. |
| 4,160,455 | A | 7/1979 | Law |
| 5,195,965 | A | 3/1993 | Shantha |
| 5,486,208 | A | 1/1996 | Glinsburg |
| 5,531,776 | A * | 7/1996 | Ward et al. .................. 607/105 |
| 5,609,591 | A | 3/1997 | Daikuzono et al. |
| 5,624,392 | A | 4/1997 | Saab et al. |
| 5,716,386 | A | 2/1998 | Ward et al. |
| 5,837,003 | A | 11/1998 | Gingsburg |
| 6,110,168 | A | 8/2000 | Ginsburg |
| 6,149,676 | A | 11/2000 | Ginsburg |
| 6,231,584 | B1 | 5/2001 | Gavronsky |
| 6,231,594 | B1 | 5/2001 | Dae |
| 6,287,326 | B1 | 9/2001 | Pecor |
| 6,290,717 | B1 | 9/2001 | Philips |
| 6,575,933 | B1 | 6/2003 | Wittenberger et al. |
| 6,607,517 | B1 | 8/2003 | Dae et al. |
| 6,641,602 | B2 | 11/2003 | Balding |
| 6,726,708 | B2 | 4/2004 | Lasheras |
| 6,746,465 | B2 | 6/2004 | Diederich et al. |
| 7,077,825 | B1 | 7/2006 | Stull |
| 7,351,254 | B2 | 4/2008 | Magers |
| 7,422,600 | B2 | 9/2008 | Dobak, III |
| 7,758,623 | B2 | 7/2010 | Dzeng et al. |
| 7,896,009 | B2 | 3/2011 | Stull |
| 8,652,190 | B2 * | 2/2014 | Stull ........................... 607/105 |
| 2003/0135252 | A1 * | 7/2003 | MacHold et al. ............. 607/106 |

OTHER PUBLICATIONS

Plattner, Olga, et al., Efficacy of Intraoperative Cooling Methods, Nov. 1997, Anesthesiology, 87:1089-1095, Nov. 1997.

Lopez, Gaston, Cold and Warm Thermoregulation by Oropharynx, Area and Esophagus, Gastroenterol Latinoam 2000; 30(3):159-64 (Abstract).

\* cited by examiner

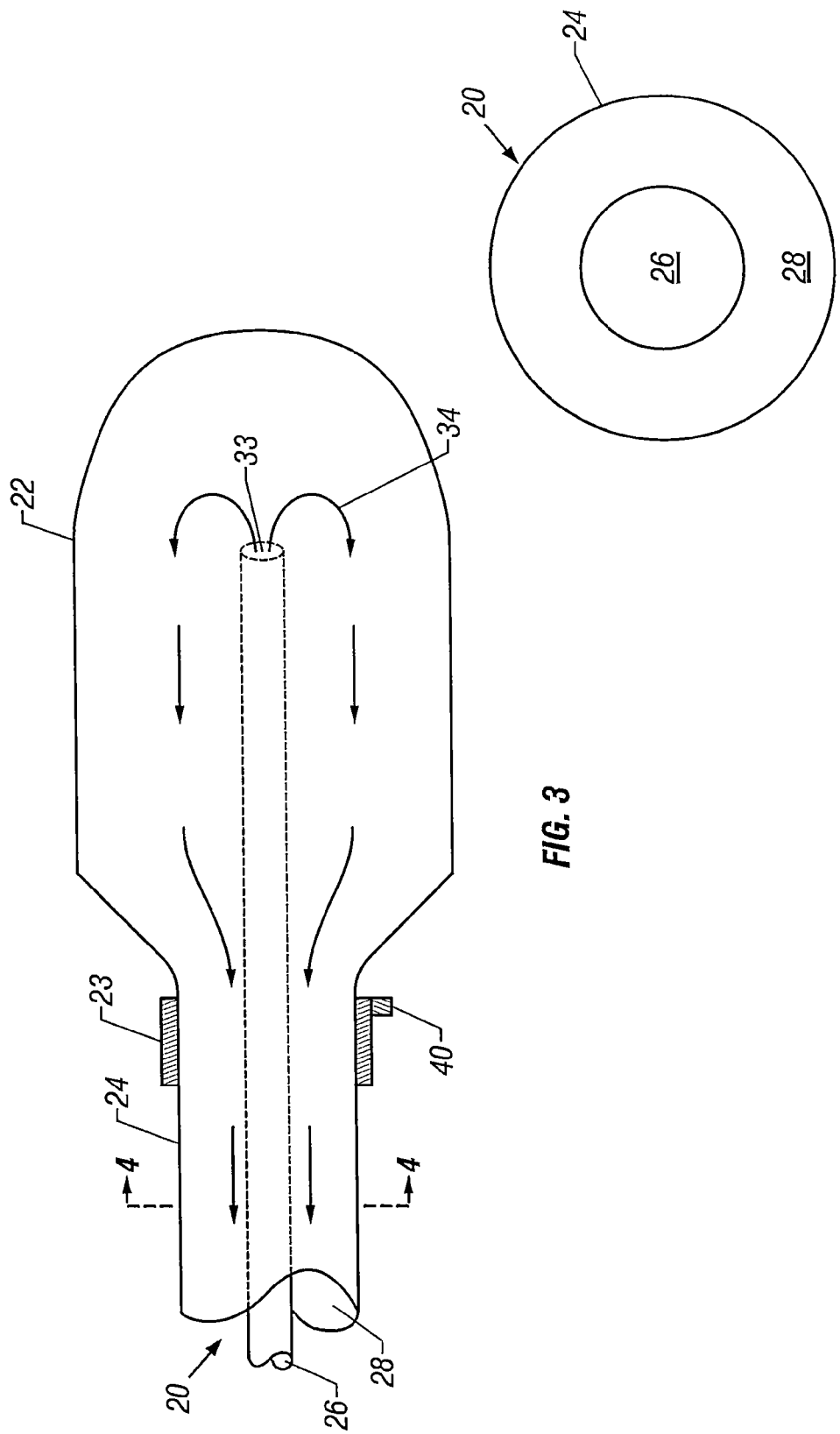

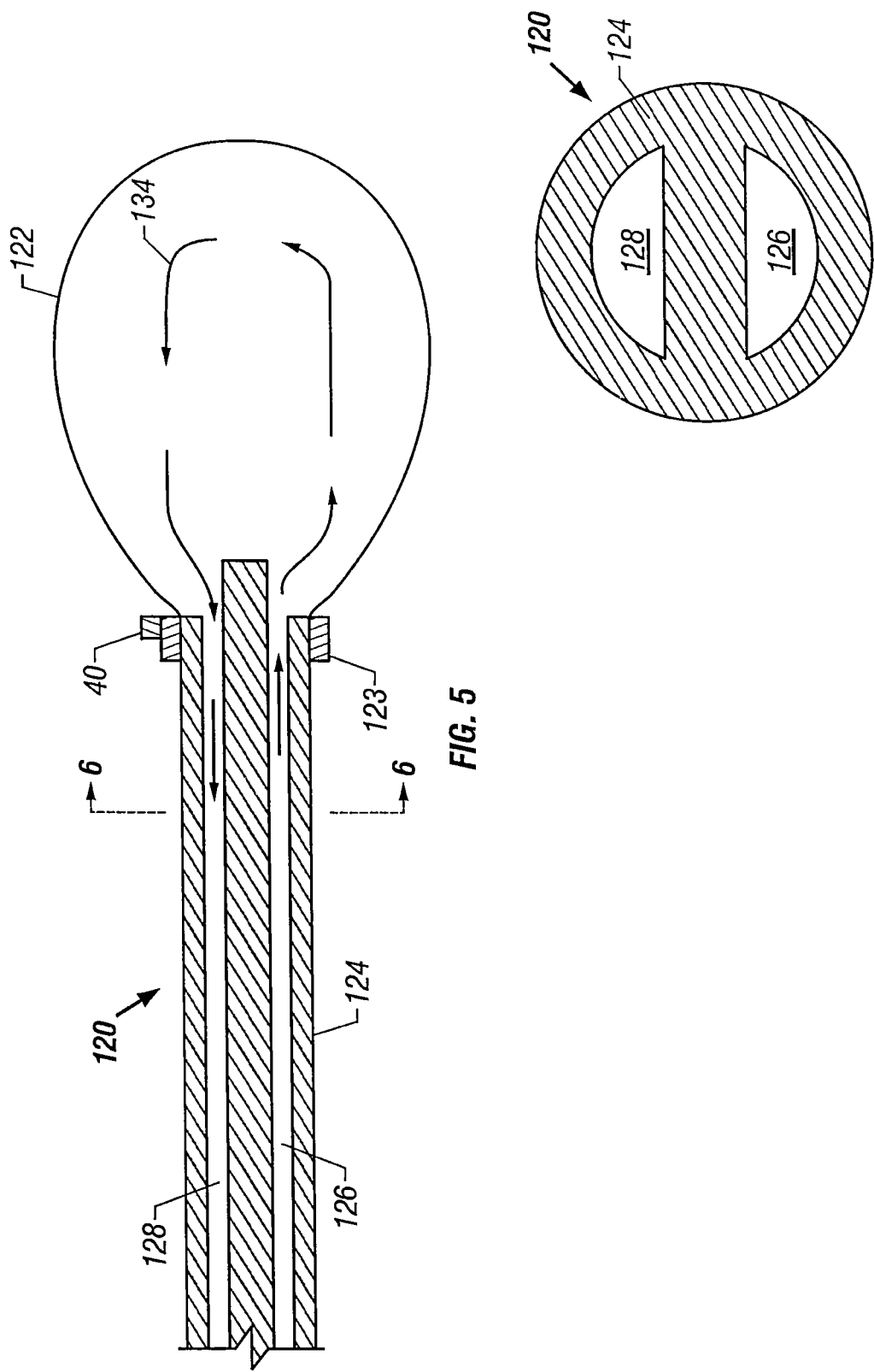
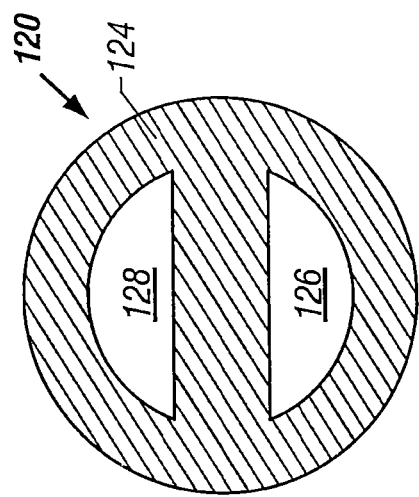
FIG. 5
FIG. 6

APPARATUS AND METHOD OF GASTRIC COOLING USING BALLOON CATHETER

This application is a continuation of U.S. application Ser. No. 13/037,224, filed Feb. 28, 2011, now U.S. Pat. No. 8,652, 190, issued Feb. 18, 2014, which is a continuation of U.S. application Ser. No. 11/474,590, filed Jun. 26, 2006, now U.S. Pat. No. 7,896,009, issued Mar. 1, 2011, which is a continuation of U.S. application Ser. No. 10/051,870, filed on Jan. 16, 2002, now U.S. Pat. No. 7,077,825, issued Jul. 18, 2006, the contents of which are hereby incorporated by reference in their entirety. Applicant claims priority to all of the applications in the chain.

This invention relates generally to apparatus and methods for the selective modification and control of body temperature by lowering, maintaining or raising the temperature of a portion of a patient's body. More particularly, the invention relates to the application of a gastric temperature control technique using a heat exchange fluid circulated through a balloon catheter.

BACKGROUND OF THE INVENTION

Normothermia is a condition of normal body temperature. Though temperature does vary at different parts of the body, the normal core body temperature of a human adult is often stated to be at 98.6 degrees Fahrenheit or 37.0 degrees centigrade. There are numerous therapeutic reasons for inducing hypothermia (a decrease in the core body temperature), or warming a hypothermic patient to normothermia, or (rarely) to hyperthermia, or inducing normothermia (approximately 37 degrees centigrade) in a patient suffering from an elevated temperature. For example, hypothermia may be induced to minimize damage to the brain or spinal cord when a patient has suffered a head injury or stroke, or to minimize damage to heart and brain tissue when a patient has undergone cardiac arrest or suffered a myocardial infarct (heart attack). Mild hypothermia has been shown to both increase the contractility of the heart muscle and to reduce its metabolic requirements. Indeed, if the hypothermia is systemic, the metabolic demands of the entire body are generally reduced, so that the demands placed on the heart may be reduced. It may sometimes also be desirable to induce hypothermia during surgery, especially neurosurgery, once again to minimize tissue damage.

Cooling is well accepted as a neuroprotectant, and may be helpful for a patient suffering ischemic insult to the brain or spinal cord, such as a stroke or trauma. It is also known that a fever significantly increases the risk of a bad neurologic outcome suffered by a stroke victim. It may therefore be beneficial to cool a stroke victim who would otherwise develop a fever.

Temperature control over a patient may affect the activity of various drugs applied to a patient for therapeutic reasons, such as chemotherapeutic drugs. A physician may wish to control such patient's temperature above or below normothermia. The temperature may also have other therapeutic value, such as reduction of inflammation, or destruction of certain infectious agents such as bacteria or viruses.

In re-warming a patient, either after therapeutic hypothermia or a patient suffering from accidental hypothermia, a very gradual and controlled re-warming rate is often desirable. The dramatic generation of metabolic heat due to shivering, particularly in addition to heat added by other means, can result in rapid and uncontrolled re-warming. A therapeutic regimen for controlling body temperature preferably does so at a carefully monitored and controlled rate.

Early techniques involved application of cold to the skin surface or cooling the inspired air, alone or in combination. However, the human body has very effective thermoregulatory responses such as areterio-venous shunts, vasoconstriction, and shivering, that generally combine to make such surface cooling and cold breathing gases ineffective to control core body temperature. In situ blood temperature modification using a heat exchange catheter system was described in U.S. Pat. Nos. 5,486,208, 5,837,003 and 6,110,168, all to Ginsburg, the disclosures of which are incorporated herein by reference in their entireties.

A method to exchange heat between a device positioned in the esophagus and a proximately located thoracic vessel, such as the descending aorta, in order to increase or decrease the temperature of the blood flowing in the vessel was described in U.S. Pat. No. 5,531,776 to Ward et al., entitled "Non-Invasive Aortic Impingement and Core and Cerebral Temperature Manipulation Method," the contents of which are incorporated herein by reference in their entirety. The device includes an esophageal balloon which can be enlarged to displace the wall of the esophagus toward the thoracic vessel. The esophageal balloon includes a heat transfer surface, and heat is exchanged between the heat transfer surface and the blood flowing through the vessel across the wall of the esophagus and the wall of the vessel. The inflation of the balloon within the esophagus, however, may block the esophagus with various problematic results, for example blockage of saliva drainage to the stomach, and may limit the duration of the temperature treatment.

Controlling body temperature through gastric lavage (which is sometimes referred to as stomach pumping) involves the cyclic application of a cooling fluid directly to the stomach. In gastric lavage, up to about 500 ml of cooled sterile water is delivered into the stomach under gravity through an orogastric tube. Some of the water is later aspirated. The direct application of fluid to the stomach, and an inability to aspirate much of the delivered water, may cause abdominal cramping, gastrointestinal irritation, and diarrhea. This method is also generally messy and not suited for use in many environments, for example hospitals or ambulances. This procedure may also be limited by the amount of fluid which may be delivered into the stomach, particularly where a patient is very sensitive to fluid overload such as a patient suffering a myocardial infarct.

Therefore, there continues to be a need to develop a convenient method of controlling body temperature, e.g., inducing hypothermia or otherwise reducing the body temperature, or gently and slowly raising the body temperature from a hypothermic state.

SUMMARY OF THE INVENTION

The stomach, especially when expanded, is a highly vascularized organ. As such, it provides an excellent location to add or remove heat from the bloodstream of a patient. A cooling catheter with a heat exchange region placed within the stomach can cool the blood flowing through the stomach which will then rapidly circulate throughout the body of a patient and thus rapidly affect the body temperature of the patient. In addition, the stomach is located in the core of the body, and any heat exchanged through conduction is directly exchanged with the core of the body and therefore avoids many of the defenses the body has that have been developed to prevent heat exchange with the external environment.

Where a balloon catheter is positioned in the stomach of a patient, heat is exchanged between the balloon catheter and the stomach so as to controllably alter the temperature of the blood flowing through the stomach. The balloon catheter may be expanded to distend the stomach and to press against the stomach lining. The heat exchange system of the balloon catheter is capable of altering the temperature of a substantial portion of the patient's body, i.e., more than just the lining of the stomach. A heat exchange fluid may be circulated in a closed-loop fashion through the balloon catheter placed in the stomach for the selective modification and control of the body temperature of the patient. By controlling the temperature of the heat exchange fluid circulated through the balloon catheter, heat can be transferred to or from blood flowing in the stomach tissue, and the core body temperature of the patient may thereby be increased or decreased.

The balloon catheter may comprise a balloon into which a heat exchange fluid is delivered through a first fluid lumen and from which the heat exchange fluid is circulated out of the balloon through a second fluid lumen. The balloon is expanded by the delivered heat exchange fluid such that heat is exchanged between the stomach and the heat exchange fluid circulating in the balloon so as to controllably increase or decrease the temperature of the blood flowing through the stomach. Where the heat exchange fluid is a cooling fluid, hypothermia may be induced in the patient. The application of mild hypothermia may increase the contractility of the heart muscle and reduce the metabolic requirements of the heart. The present invention may also be used for the controlled re-warming of the patient.

In one embodiment of the invention, a temperature probe that senses the temperature of the patient provides feedback by which the rate of heat exchange between the balloon catheter and the blood in the stomach may be controlled. For example, to reduce the rate of cooling, the temperature of the heat exchange fluid may be increased, or the rate of circulation may be reduced. This may be automatically achieved in response to the temperature signal from the probe.

It is also the case that the human patient may respond to cooling by the thermoregulatory response of shivering. The human shivering threshold is generally about 35.5° C., a temperature below which the patient begins to shiver. In order to combat the body's natural tendency to generate additional heat through shivering, anti-shivering agents may be used. The anti-shivering agents may include agents as simple as a warming blanket, or may include various drugs. A method to combine cooling with anti-shivering agents is disclosed in U.S. Pat. No. 6,231,594 to Dae et al., the complete disclosure of which is incorporated herein by reference.

The heat exchange catheter system may further include an external heat exchange unit for heating or cooling the heat exchange medium. This external heat exchange unit may further comprise a pumping mechanism for circulating the heat exchange fluid through the heat exchange catheter. The external heat exchange unit may also be controlled by a control unit that may control the temperature to which the circulating heat exchange fluid is adjusted, the rate at which the heat exchange fluid is circulated, or other parameters that may affect the rate of heat exchange between the catheter and the patient's bloodstream. The controller may receive input from the temperature sensor mentioned above, and may control the rate of heat exchange between the catheter and the patient's bloodstream in response to said input.

Various suitable controllers and external heat exchangers may be used. For example, the controller and heat exchanger as disclosed in U.S. patent application Ser. No. 09/138,830 to Machold et al.; Ser. No. 09/563,946 to Machold et al.; and Ser. No. 09/707,257 to Machold et al. Another system for controlling the body temperature of a patient is disclosed in patent application Ser. No. 09/938,851, entitled "Method of Inotropic Treatment of Circulatory Failure Using Hypothermia," the contents of which are hereby incorporated by reference in their entirety.

Further aspects of the present invention will become apparent to those of skill in the art upon reading and understanding of the detailed description and examples set forth below.

BRIEF DESCRIPTION OF THE DRAWINGS

FIG. 3 is a sectional view of a portion of an embodiment of the balloon catheter for use in the invention.

FIG. 4 is a cross-sectional view of the catheter shaft through lines 4-4 of FIG. 3.

FIG. 5 is a sectional view of a portion of an alternate embodiment of the balloon catheter for use in the invention.

FIG. 6 is a cross-sectional view of the catheter shaft through lines 6-6 of FIG. 5.

DETAILED DESCRIPTION OF THE PREFERRED EMBODIMENTS

Figure 1:
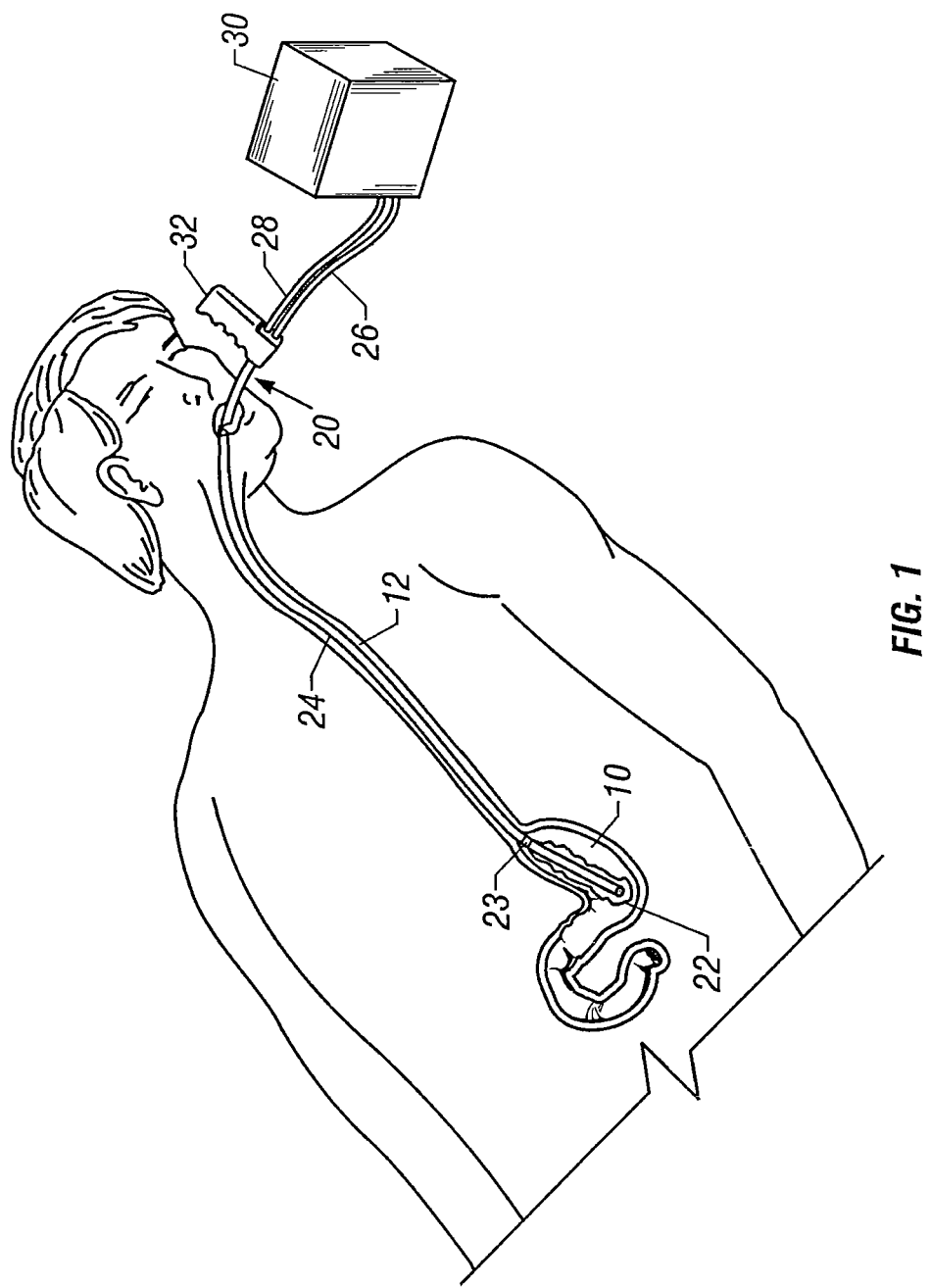
FIG. 1 is a depiction of an embodiment of the balloon catheter in place in a patient with a heat exchange unit for practicing the invention.

As shown in the exemplary drawings, the invention is directed toward a non-invasive gastric apparatus and method of cooling, or otherwise manipulating, the body temperature of a patient using a balloon catheter. As used herein, like reference numerals will designate similar elements in the various embodiments of the present invention to be discussed. The invention will be described in relation to the use of a heat exchange fluid circulating within a balloon catheter placed within the stomach of a patient to induce hypothermia, or otherwise control the body temperature of the patient. It is to be understood, however, that the invention is not so limited. For example, although the invention will be described as using a heat exchange fluid, it is to be understood that other heat exchange mechanisms can be used.

Hypothermia is preferably induced in a manner fast and efficient enough to cool the patient without undue stress. Hypothermia may be induced by using a catheter that circulates heat exchange fluid through a heat exchange region (e.g., a balloon), and circulating the heat exchange fluid through an external heat exchanger to adjust the temperature of the heat exchange fluid and then recirculating the heat exchange fluid through the heat exchange region of the balloon. This circulation is continuous, preferably in a closed circuit, exchanging heat from the surrounding tissue into the heat exchange fluid, and then out of the heat exchange fluid in the external heat exchanger for a sufficient length of time to cool the patient to achieve the desired advantages of this invention.

Inducing hypothermia has many advantages. For example, in a patient suffering from circulatory failure, including congestive heart failure, inducing hypothermia increases the contractility of the cardiac muscle cells, similar to an inotropic drug, while at the same time reducing the metabolic oxygen requirements of those same muscle cells. If the hypothermia delivered is systemic, the metabolic requirements and waste products of the entire body are reduced, which reduces the overall demands on the heart.

The general method of the invention may comprise using a gastric cooling device such as a cooling balloon catheter to: induce hypothermia in the patient; maintain the patient in the hypothermic condition for a sufficient time to provide a therapeutic benefit; and re-warm the patient in a controlled manner. The same heat exchange system used to induce the hypothermia may be used to re-warm the patient. More specifically, the patient may be cooled to a temperature between 32° C. and 36° C., maintained at that cooled temperature for a period of three hours, six hours, or even a day or more, and then re-warmed to normothermia, generally 36.5° C. to 37° C. Generally the warming is slow and controlled, sometimes as slow as 0.2° C./hour.

The method may also be practiced with automatic control over the heat exchange mechanism that is inducing and maintaining hypothermia. A temperature probe that senses the temperature of the patient provides a signal to an automatic controller that, in response to that signal representing the measured temperature, controls the hypothermic state of the patient. The patient's temperature may be under the control of an automatic temperature control system governed by a signal from a temperature probe in or on the patient's heart, esophagus, blood stream, tympanic membrane, skin, or other area that will deliver a signal that is representative of the core temperature of the patient.

The method may additionally include the steps of: administering an anti-shivering agent; automatically controlling the patient's temperature using feedback from a temperature probe on or in the patient; and re-warming the patient, perhaps at a very slow and controlled rate. To prevent shivering, a warming blanket and various anti-shivering drugs may be used either alone or in combination. The anti-shivering regime is generally started before the patient is cooled below the shivering threshold.

As illustrated in FIG. 1, the balloon catheter 20 is introduced through the esophagus 12 and delivered into the stomach 10 of a patient with the balloon 22 deflated. The entire balloon 22 is located within the stomach 10, and the catheter shaft 24 is located within the esophagus 12 of the patient. The distal end of the catheter shaft 24 may further include radiopaque markers adjacent to the proximal end of the balloon 22 to identify when the balloon 22 is positioned fully within the stomach 10 of the patient. A sheath (not shown) may be wrapped around the deflated balloon at the distal end of the catheter shaft in order to assist in maintaining a small delivery profile for the catheter. Such a sheath may include perforations to allow the balloon to expand upon inflation by fluid delivered through the catheter shaft 24.

The shaft 24 of the balloon catheter 20 may have a coaxial lumen configuration, a side-by-side (or dual) lumen configuration, or any other suitable lumen configuration to allow the ingress and egress of a heat exchange fluid to and from the balloon 22. The heat exchange fluid is supplied through an inlet 26 and returned through an outlet 28 in a closed-loop fashion. A heat exchange unit 30 circulates the heat exchange fluid to the balloon catheter 20 as part of a closed-loop system. The heat exchange unit 30 controls the temperature of the heat exchange fluid, and can maintain the heat exchange fluid at a constant temperature for an extended period of time. The balloon catheter 20 may further include a handle 32 to assist in positioning the balloon catheter in the stomach 10 of the patient. The balloon catheter 20 may be disposably attached to the heat exchange unit 30 at the handle 32.

Figure 2:
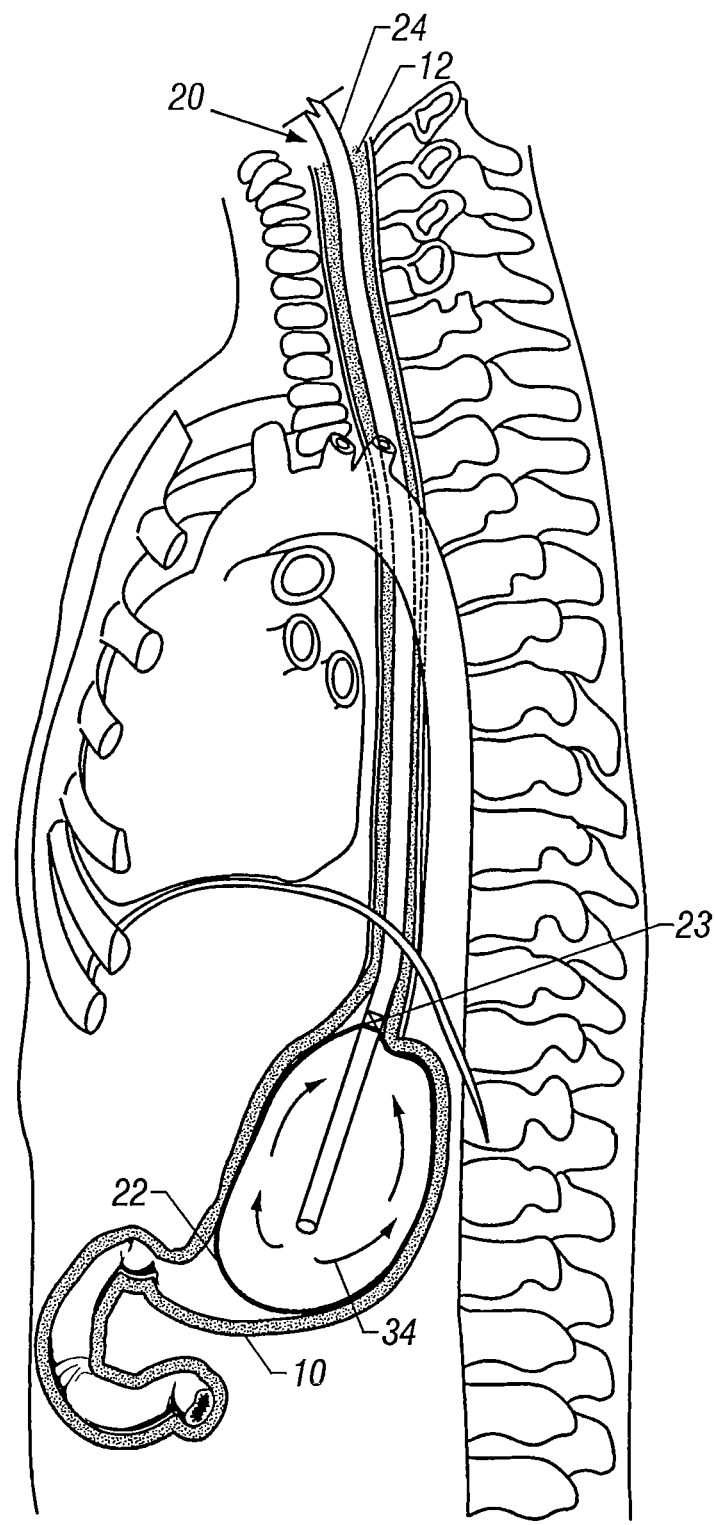
FIG. 2 is a sectional side elevation view illustrating the chest cavity of a patient and showing an embodiment of the balloon catheter for practicing the invention in an operative position.

As illustrated in FIG. 2, after introduction of the balloon catheter 20 into the stomach 10 of the patient, the balloon 22 may be expanded to occupy the entire volume of the stomach 10. The stomach 10 substantially conforms around the inflated balloon 22 so that substantially the entire surface area of the balloon 22 is in contact with the wall of the stomach 10. The balloon is preferably sized to correspond generally to the approximate size and shape of a slightly distended stomach upon expansion of the balloon.

The heat exchange fluid 34 is introduced into the balloon 22 through an opening 33 formed in the distal end of the catheter shaft 24. The introduction of the heat exchange fluid 34 expands the balloon 22 to fill the volume of the stomach 10. The heat exchange fluid 34 circulates within the balloon 22 (as denoted by the arrows), and flows out of the balloon 22, back through the catheter shaft 24, and is then returned to the heat exchange unit. The details of this closed-loop circulation of the heat exchange fluid will be discussed in more detail later. Because the heat exchange fluid is circulated in a closed-loop, the heat exchange fluid does not come into contact with either the stomach or the bloodstream, so the heat exchange fluid need not be a physiologic fluid such as saline. The heat exchange fluid 34 may be a gas or a liquid. However, in the event of a rupture of the balloon some of the heat exchange fluid would enter the digestive tract, so the heat exchange fluid should be non-toxic. Since physiological saline is a generally acceptable heat exchange fluid in the preferred temperature ranges, it is a generally acceptable heat exchange fluid in the embodiment described here. The heat exchange fluid 34 is circulated within the balloon 22, preferably for an extended period of time (ranging from several hours to several days), in order to exchange heat between the circulating heat exchange fluid 34 and the blood circulating through the vessels surrounding the wall of the stomach 10 in order to control the body temperature of the patient. The balloon 22, inflated with the circulating heat exchange fluid 34, acts as a heat exchange region. The temperature of the circulated heat exchange fluid 34 may be significantly higher (for heating) or significantly lower (for cooling) than the normal body temperature. The heat exchange fluid 34 may be maintained at a constant predetermined temperature such as zero degrees centigrade, or colder, for an extended period of time. It is also contemplated that a patient's temperature may be reduced by this relatively non-invasive technique over a short period of time in, for example, an ambulance or an emergency room, and, subsequently, more invasive temperature control may be instituted in, for example, a hospital or cath lab.

Where the heat exchange fluid circulated through the balloon 22 is colder than the core body temperature, and, in particular, blood in the vessels surrounding the stomach, heat will be exchanged between the blood and the heat exchange fluid through the wall of the balloon 22 and the wall of the stomach, such that heat is absorbed from the blood. If the temperature difference between the blood and the heat exchange fluid (sometimes called "ΔT") is large enough (for example, if the blood of the patient is about 37° C., and the temperature of the heat exchange fluid is about 0° C.), enough heat may be exchanged to cool the temperature of the blood sufficiently for therapeutic purposes. Heat will also be exchanged with the core by conduction, and since the body core is liquid, largely water, heat is conducted fairly efficiently out of the core and into the heat exchange fluid. If the balloon catheter is left in place long enough with the cold circulating heat exchange fluid, the entire body temperature of the patient may be cooled sufficiently to reduce the metabolism of the body and reduce the demands placed on the heart.

The diameter of the catheter shaft 24 is smaller than the diameter of the esophagus 12. The catheter shaft 24 is sized to provide sufficient clearance within the esophagus 12 so as to not block saliva drainage in the esophagus 12 while the heat exchange fluid 34 is being circulated within the balloon catheter 20. While there may be a need to deal with the gag response during the insertion of the balloon catheter, whether by sedation or otherwise, this generally will not be a problem after the balloon catheter is in place. Insertion of the balloon catheter may be facilitated by allowing the patient to drink some liquid during the insertion. Once the deflated balloon is "swallowed," the catheter shaft is in place and has a sufficiently small diameter so as not to block the esophagus. The natural swallowing motion of the throat will serve to insure that the balloon portion is fully located in the stomach.

The distal portion of one embodiment of the balloon catheter 20 is illustrated in FIG. 3. The balloon catheter 20 is shown as having a coaxial lumen configuration in FIGS. 3 and 4, but it is to be understood that a side-by-side or dual lumen configuration may also be employed. The catheter shaft 24 having a coaxial lumen configuration includes an inflow lumen 36 and an outflow lumen 38. At the proximal end of the catheter 20, the inflow lumen 36 is in fluid communication with the inlet 26 leading from the heat exchange unit 30, and the outflow lumen 38 is in fluid communication with the outlet 28 leading to the heat exchange unit 30. The heat exchange fluid 34 flows into the balloon 22 through the distal opening 33 of the inflow lumen 36 in the catheter shaft 24 to inflate the balloon 22. The heat exchange unit preferably introduces the heat exchange fluid 34 at a sufficient pressure to maintain the inflated balloon 22 at the approximate size of the stomach 10 while allowing the heat exchange fluid to 34 circulate out of the balloon 22 through the outflow lumen 38 and outlet 28, and back to the heat exchange unit 30.

The catheter shaft 24 is preferably constructed from a biocompatible, flexible material having suitable column strength such as PEBAX. Polyether block amides, sometimes referred to as PEBAX, are a family of thermoplastic polyether-based polyamides often used for catheters with various multi-lumen profiles. The processing of such materials for the fabrication of such catheters is well known in the art.

The balloon 22 is attached to the catheter shaft 24 by a balloon attachment 23 which is well known in the art. The balloon attachment 23 may be radiopaque, or visible to ultrasound, to act as a marker and allow an operator to determine when the balloon is fully positioned within the stomach 10. In the alternative, a marker separate from the balloon attachment 23 may be used. A temperature sensor 40 may also be located in the area of the balloon attachment 23.

The material for the balloon 22 preferably is a thin-walled, high strength, thermoplastic material, readily inflatable under fluid pressure and readily collapsible under vacuum. In this embodiment, the balloon 22 is made from polyethylene terephthalate (PET). The balloon 22 should be dimensioned to conform generally with the stomach 10. Upon expansion, the balloon 22 should approximate the size and shape of the slightly distended stomach 10. The balloon 22 is expanded by the introduction of the heat exchange fluid 34. The act of slightly distending the stomach may trigger increased blood flow through the stomach lining and enhance the heat exchange. Upon completion of the heat exchange procedure, the balloon 22 may be collapsed by applying a vacuum to evacuate the heat exchange fluid 34 from the balloon 22.

Where the balloon 22 is composed of a substantially inelastic material, the inflow lumen 38 preferably extends substantially into the interior of the balloon 22. The balloon 22, when deflated, may be wrapped around the distal portion of the inflow lumen 38, and may be held in place by a sheath (not shown), to create a low delivery profile for the balloon catheter 20.

In an alternate embodiment, as illustrated in FIG. 5, the balloon catheter 120 may include an elastic balloon 122 made from an elastic material such as latex or polyurethane. The elastic balloon 122 may be fastened to the catheter shaft 124 by an attachment 123 known in the art. The balloon attachment 123 may be radiopaque, or opaque to ultrasound, to act as a marker and allow an operator to determine when the balloon is fully positioned within the stomach of the patient. In the alternative, a marker separate from the balloon attachment 123 may be used. A temperature sensor 40 may also be located in or near the area of the balloon attachment 23.

Although FIGS. 5 and 6 show the shaft 124 of the balloon catheter 120 as having a side-by-side (or dual) lumen configuration, it is to be understood that a coaxial lumen configuration may also be employed. The catheter shaft 124 having a side-by-side lumen configuration includes an inflow lumen 136 and an outflow lumen 138. The catheter shaft 124 is preferably constructed from PEBAX or another suitable material. At the proximal end of the catheter 120, the inflow lumen 136 and the outflow lumen 138 are in separate fluid communication with the heat exchange unit. The heat exchange fluid 134 flows into the balloon 122 through the inflow lumen 136 to inflate the balloon 122. Because the balloon 122 in this embodiment is elastic, the lumen of the catheter shaft 124 need not extend substantially into the interior of the balloon 122, and a sheath may not be needed to maintain a low profile for the balloon portion of the catheter 120. The heat exchange unit preferably introduces the heat exchange fluid 134 at a sufficient pressure to maintain the inflated balloon 122 at the approximate size of the stomach while allowing the heat exchange fluid 134 to circulate out of the balloon 122 through the outflow lumen 138 and back to the heat exchange unit. Upon completion of the heat exchange procedure, the elasticity of the balloon may aid in the evacuation of the heat exchange fluid and the collapsing of the balloon.

Figure 7:
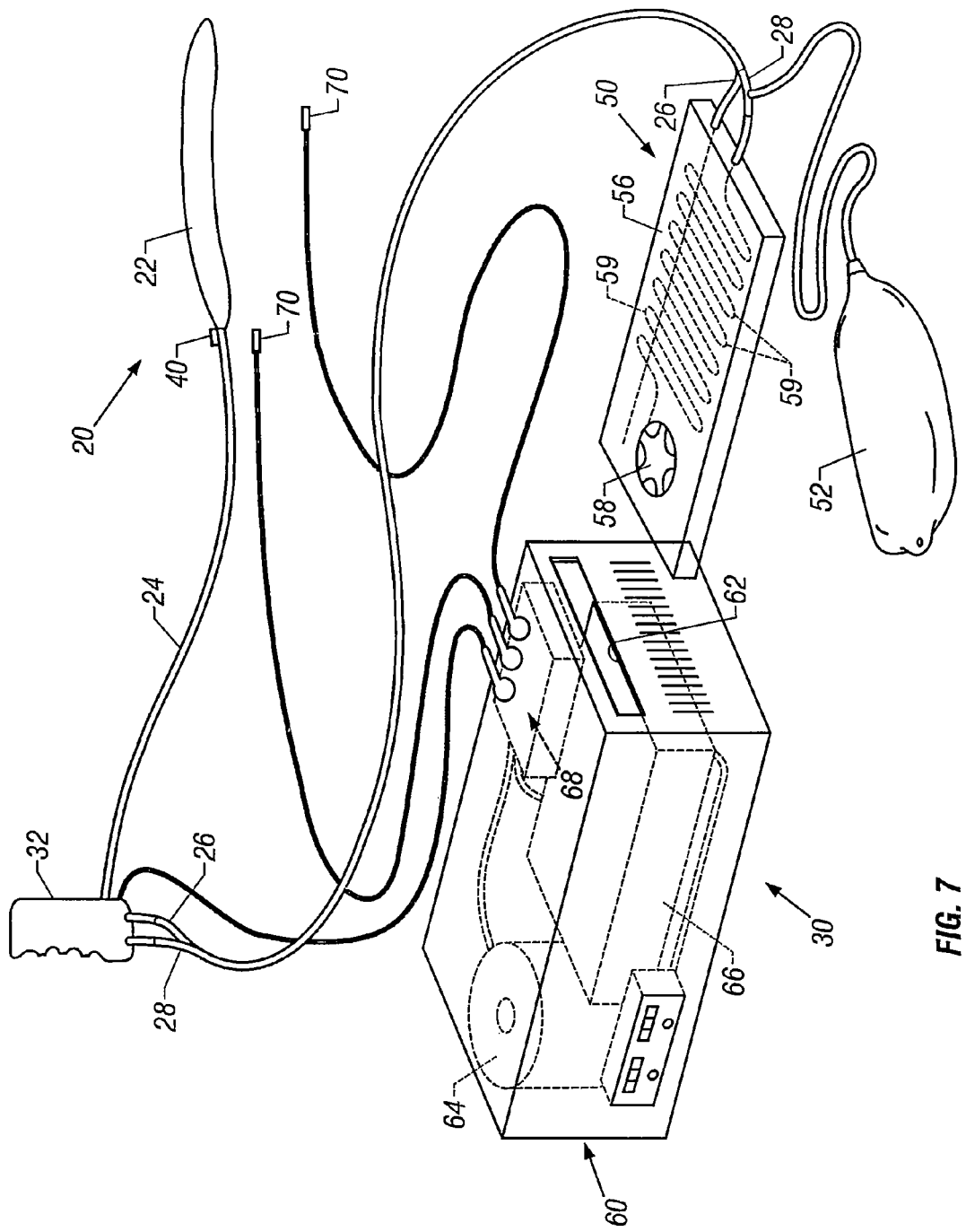
FIG. 7 is a depiction of an embodiment of the balloon catheter and heat control unit for use in the invention.

One embodiment of the system for controlling the heat exchange by the balloon catheter is illustrated in FIG. 7. The temperature of the heat exchange fluid circulated within the balloon catheter 20 is controlled by the heat exchange unit 30. In this embodiment, the heat exchange unit 30 includes a disposable heat exchanger cassette 50 and a control unit 60 for controlling the temperature of the heat exchanger cassette 50. The control unit 60 receives a signal transmitted from a temperature sensor such as a temperature probe inserted in the patient's vasculature to provide an accurate measure of the core temperature of the patient. Other suitable temperature sensors may include bladder temperature probes, tympanic temperature probes, rectal temperature probes, or properly situated skin temperature sensors.

The disposable heat exchanger cassette 50 includes a saline bag 52 connected to the outlet 28 of a multi-lumen fluid conduit extending from the heat exchange element 50, a heat exchange plate 54, a pump head 56, and a fluid pathway 58. As previously discussed, the heat exchange region is the balloon 22 inflated by the closed-loop flow of the heat exchange fluid. The handle 32 of the balloon catheter 20 includes a connection for the inlet 26, and a connection for the outlet 28 from the fluid conduit 54. As previously discussed, the inlet 26 and the outlet 28 are in fluid communication with the respective inflow and outflow lumina of the multi-lumen catheter shaft 24. The saline bag 52 operates as an external fluid source, and may be placed in fluid communication with the outlet 28 at a T-junction of the fluid conduit. In the alternative, the external fluid source may be directly connected to the heat exchanger cassette 50. The pump head 56 pumps the heat exchange fluid from the saline bag 52 through a fluid pathway 58 in the heat exchange plate 54, and then through to the balloon catheter via the inlet 26.

The heat exchange unit 50 may be configured to fit through an elongate slot 62 in the control unit 60. Other configurations are possible, depending on the requirements of the system design. Once inserted, the pump head 56 is placed in proximity to and couples with the pump driver 64, generally either with a mechanical engagement or a magnetic coupling, and the heat exchange plate 54 is placed in proximity to and in thermal communication with a heat exchanger 66. In one embodiment, the heat exchanger 66 is a solid-state thermoelectric heater/cooler device capable of either generating heat or removing heat by changing the polarity of the current activating the unit. The heat exchanger 66 may be controlled so as to supply or remove heat from the system without the need for two separate units. In the alternative, a cardiopulmonary bypass heat exchanger immersed in an ice-and-water slurry may be utilized.

The pump driver 64 engages and activates the pump head 56 to circulate the heat exchange fluid through the serpentine fluid pathway 58 in the heat exchange plate 54. The heat exchanger 66 may act to heat or cool the heat exchange fluid circulated through the serpentine fluid pathway 58, and thereafter through the inlet 26 and inflow lumen of the balloon catheter 20. The heat exchanger 66 regulates the blood temperature of the patient as desired by circulating the heat exchange fluid through the balloon 22 at the heat exchange region in order to add or remove heat from the body of the patient.

The pump driver 64 and heat exchanger 66 are responsive to the controller processor 68. The processor 68 receives data input from sensors such as body temperature sensors 70 positioned to sense the temperature at various locations of the patient. For example, the temperature may be sensed at the patient's ear, heart region, bladder, rectum, esophagus, upper thigh or another appropriate location as desired by the operator. The processor 68 may also receive data from a temperature sensor 40 provided on or adjacent to the balloon portion 22 of the balloon catheter 20 to monitor the temperature of the heat exchange region in the stomach of the patient. Operating parameters of the control system, such as the desired body temperature of the patient or the desired temperature of the heat exchange fluid, may also be manually input by the operator.

The controller processor 68 coordinates the various data received and selectively actuates the several operational subsystems to achieve and maintain a desired body temperature for the patient. For example, the processor 68 may actuate the heat exchanger 66 to increase the amount of heat being removed from the heat exchange fluid if the actual temperature is above the specified temperature, or the processor 68 may decrease the amount of heat being removed if the temperature is below the specified temperature. In the alternative, the processor 68 may control the speed of the pumping of the heat exchange fluid.

In operating the heat exchange unit 30, the disposable heat exchanger cassette 50 is inserted into the control unit 60, and the external fluid source 52 is attached to the appropriate port of the heat exchanger cassette 50, and the pump 56 is automatically or passively primed. Chilled or warmed biocompatible fluid such as saline, may be pumped into the closed circuit balloon catheter, which exchanges heat directly with the blood flowing around the stomach of the patient. The control unit 60 serves to automatically control the patient's temperature. Once treatment with the balloon catheter 20 is complete, the balloon catheter 20 is deflated and then removed from the patient, and the heat exchanger cassette 50 is removed from the reusable control unit 60. Both the balloon catheter 20 and heat exchanger cassette 50 may then be discarded. The control unit does not come into direct contact with the heat exchange fluid, and may be used immediately thereafter for treatment on other patients with a new disposable heat exchanger cassette and balloon catheter.

Other examples of systems for the automated control of a patient's body temperature are described in U.S. Pat. No. 6,149,676; and co-pending U.S. patent application Ser. Nos. 09/138,830, 09/563,946 and 09/707,257, the entireties of which are expressly incorporated herein by reference. In addition, the heat exchange fluid may be cooled by passing the fluid through a cardiopulmonary bypass heat exchanger immersed in an ice-and-water slurry.

If the patient is cooled below the shivering threshold (which varies for each patient, but generally is at about 35.5° C.) some mechanism should be used to combat shivering. Methods of combating shivering while cooling a patient are described in detail in U.S. Pat. No. 6,231,594, which is hereby incorporated by reference in its entirety. For example, if a patient is cooled below his or her shivering threshold, which is the temperature at which a patient, absent application of anti-shivering mechanisms, would shiver, then a warming blanket might be applied, alone or in conjunction with various anti-shivering drugs. A typical therapeutic regime may include the steps of: administering an initial bolus dose of a first anti-thermoregulatory response agent to the patient (e.g., an oral dose of a serotonin 5HT1a receptor agonist such as 60 mg of buspirone); administering a subsequent dose of a second anti-thermoregulatory response agent to the patient (e.g., an initial intravenous dose of an µ opioid receptor agonist such as 50 mg meperidine administered by slow push followed by a similar second dose); and administering a further dose of the second anti-thermoregulatory response agent by constant IV administration (e.g., about 25 mg/hour of meperidine). Another anti-shivering drug that may be useful is dexmedetomidine. A warming blanket may be wrapped around the patient when the first anti-thermoregulatory response agent is administered. Application of warmth to the patient's face may also be effective. Once the anti-thermoregulatory response mechanism is operating, cooling the patient to a temperature below the shivering threshold may be accomplished.

A patient with mild cardiac insufficiency may benefit from a period of hypothermia. For example, the method of treatment may begin with the application of anti-shivering mechanisms, such as the application of anti-shivering drugs and the application of a warming blanket. The warming blanket may not be turned on or may be turned on low at the outset, and the power of the blanket increased as the temperature of the patient is lowered. The balloon catheter is then introduced into the stomach and inflated with the heat exchange fluid to begin cooling the patient to a desired temperature such as 32° C. Depending on the condition of the patient and the therapeutic response, the temperature may be significantly higher, for example 35° C., but will usually not go below 30° C. since the heart begins to be sensitive and irritable below that temperature. The temperature of the patient is cooled at the desired level for a length of time sufficient to provide a therapeutic benefit. For example, the patient's temperature may be controlled by maintaining the desired temperature of 32° C. within 0.2° C. for several hours, usually more than four hours and sometimes more than one day. During this time the condition of the patient would be monitored, both to identify and respond to any problem, for example to increase the patient's temperature if he or she begins to exhibit symptoms that will be relieved by increases in body temperature, and to follow the patient's response to treatment to keep the length of cooling as short and mild as possible to minimize the use of anti-shivering drugs.

Patients may be given hypothermic heart "holidays" for periods of 3 hours, 12 hours, or even up to three days or longer, depending on the condition and needs of an individual patient. When the patient is placed in a hypothermic condition, such as 1° C. or more below normothermic, and the output of the heart increases, the overall condition of the patient can improve significantly. The heart may receive sufficient additional blood and have a temporarily decreased metabolic need and decreased metabolic waste products in order to recover to a healthier state.

The patient is then slowly re-warmed to normothermia (usually 37° C.) using controlled re-warming. For example, re-warming at the rate of 0.2° C. may avoid injury that might occur with too rapid re-warming. Depending on the condition of the patient and the disease being addressed, re-warming at some other rate, for example, 0.4° C. per hour, half a degree an hour, or even a degree or more, might be appropriate. The re-warming may be active (i.e., the balloon temperature is greater than the core body temperature so that the system is actively adding heat to the patient's body) or may actually be slow cooling, that is where the balloon temperature is only slightly below the core body temperature so that the system is removing heat from the body but at a rate that is slower than the body is generating heat, resulting in a slow increase in core body temperature.

A patient may also be maintained at hypothermia during a surgical procedure since the hypothermia is both inotropic and tissue protective. After the surgery, the patient may be maintained at the hypothermic level for an extended period of time, for example three hours, and then slowly and controllably warmed back to normothermia, for example at 0.5° C. per hour.

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, while remaining within the scope of the present invention. Additionally, reference to the terms such as "device," "apparatus," and terms of similar import in the claims which follow shall not be interpreted to invoke the provisions of 35 U.S.C. §112, paragraph 6, unless reference is expressly made to the term "means" followed by an intended function.

What is claimed is:

1. A heat exchange apparatus for removing from or adding heat to a stomach of a patient, comprising:
   a heat transfer catheter insertable into the stomach of a patient, the heat transfer catheter having a first fluid lumen having a distal end and a second fluid lumen having a distal end;
   an expandable balloon in fluid communication with the distal end of the first fluid lumen and the distal end of the second fluid lumen, the balloon sized such that the balloon distends the stomach when the balloon is expanded, wherein a heat exchange fluid is delivered into the balloon through the first fluid lumen and the heat exchange fluid is circulated out of the balloon through the second fluid lumen;
   a heat exchanger in fluid communication with the first fluid lumen and the second fluid lumen;
   a pump head in fluid communication with the first fluid lumen and the heat exchanger, the pump head configured to pump fluid through a fluid circuit formed by the heat exchanger, the first fluid lumen, the expandable balloon, the second fluid lumen and the heat exchanger;
   a master control unit housing a pump driver and a heater/cooler unit within and having a slot, the slot being sized so that the heat exchanger can be installed therethrough into the master control unit and into thermal communication with the heater/cooler unit, the pump driver engaging the pump head when the heat exchanger is installed through the slot; and
   wherein heat is exchanged between the stomach and the heat exchange fluid circulating in the balloon so as to controllably alter the temperature of at least a portion of the patient.

2. The apparatus according to claim 1, wherein the balloon comprises a thin-walled, high strength, thermoplastic material, readily inflatable under fluid pressure and readily collapsible under vacuum.

3. The apparatus according to claim 1, wherein the material of the balloon comprises polyethylene terephthalate.

4. The apparatus according to claim 1, wherein the balloon is expandable to approximate the shape of the stomach.

5. The apparatus according to claim 1, wherein the balloon comprises an elastic material.

6. The apparatus according to claim 1, wherein the balloon is configured to generally conform with the stomach when the balloon is expanded.

7. The apparatus according to claim 1, wherein the first fluid lumen is coaxial with the second fluid lumen.

8. The apparatus according to claim 1, wherein the first fluid lumen is side-by-side with the second fluid lumen.

9. The apparatus according to claim 1, wherein when the balloon is expanded by the delivered heat exchange fluid, the expanded balloon substantially conforms with the stomach.

10. The apparatus according to claim 1, further comprising a temperature sensor located adjacent to the balloon.

11. The apparatus according to claim 1, further comprising a thermoelectric heat exchanger connected to the first fluid lumen, wherein the thermoelectric heat exchanger controls the temperature of the heat exchange fluid flowing to the first fluid lumen.

12. The apparatus according to claim 11, wherein the thermoelectric heat exchanger includes a temperature probe, and the thermoelectric heat exchanger is automatically controlled based on signals received from the temperature probe.

* * * * *